United States Patent [19]

Partridge, Jr. et al.

[11] Patent Number: 5,277,881
[45] Date of Patent: Jan. 11, 1994

[54] HYDROGEN FLUORIDE ALKYLATION APPARATUS AND VAPOR RECOVERY METHOD

[75] Inventors: George P. Partridge, Jr., Orange; Kenneth R. Comey, III; James Mudra, IV, both of Beaumont; Lee K. Gilmer, Nederland, all of Tex.

[73] Assignee: Texaco Inc., White Plains, N.Y.

[21] Appl. No.: 944,619

[22] Filed: Sep. 14, 1992

[51] Int. Cl.$^5$ .............................................. B01J 19/00
[52] U.S. Cl. .................................... 422/241; 422/240; 422/255; 585/723; 585/724; 585/725
[58] Field of Search ............... 422/240, 241, 255, 256, 422/228; 585/723, 724, 725

[56] References Cited

U.S. PATENT DOCUMENTS

| | | | |
|---|---|---|---|
| 2,391,148 | 12/1945 | Frey | 585/725 |
| 4,218,574 | 8/1980 | Anderson | 585/723 |
| 4,220,806 | 9/1980 | Mikulicz et al. | 585/723 |
| 4,225,561 | 9/1980 | Torres | 422/180 |
| 4,243,830 | 1/1981 | Carson | 585/723 |
| 4,467,131 | 8/1984 | Washer et al. | 585/723 |
| 4,555,325 | 11/1985 | Wolowski et al. | 422/241 |
| 4,891,466 | 1/1990 | Kocal | 585/725 |
| 4,938,935 | 7/1990 | Audeh et al. | 585/725 |
| 4,938,936 | 7/1990 | Yan | 585/725 |
| 5,073,674 | 12/1991 | Olah | 585/725 |

Primary Examiner—Robert J. Warden
Assistant Examiner—Hien Tran
Attorney, Agent, or Firm—James L. Bailey; Richard A. Morgan

[57] ABSTRACT

A safety apparatus has been found for controlling the release of flashing hydrogen fluoride in a hydrocarbon alkylation process. The safety apparatus comprises containment baffles enclosing major process vessels. The safety apparatus may be used in combination with a liquid onium polyhydrogen fluoride complex to substantially reduce the vapor cloud produced from a leaking process vessel.

13 Claims, 1 Drawing Sheet

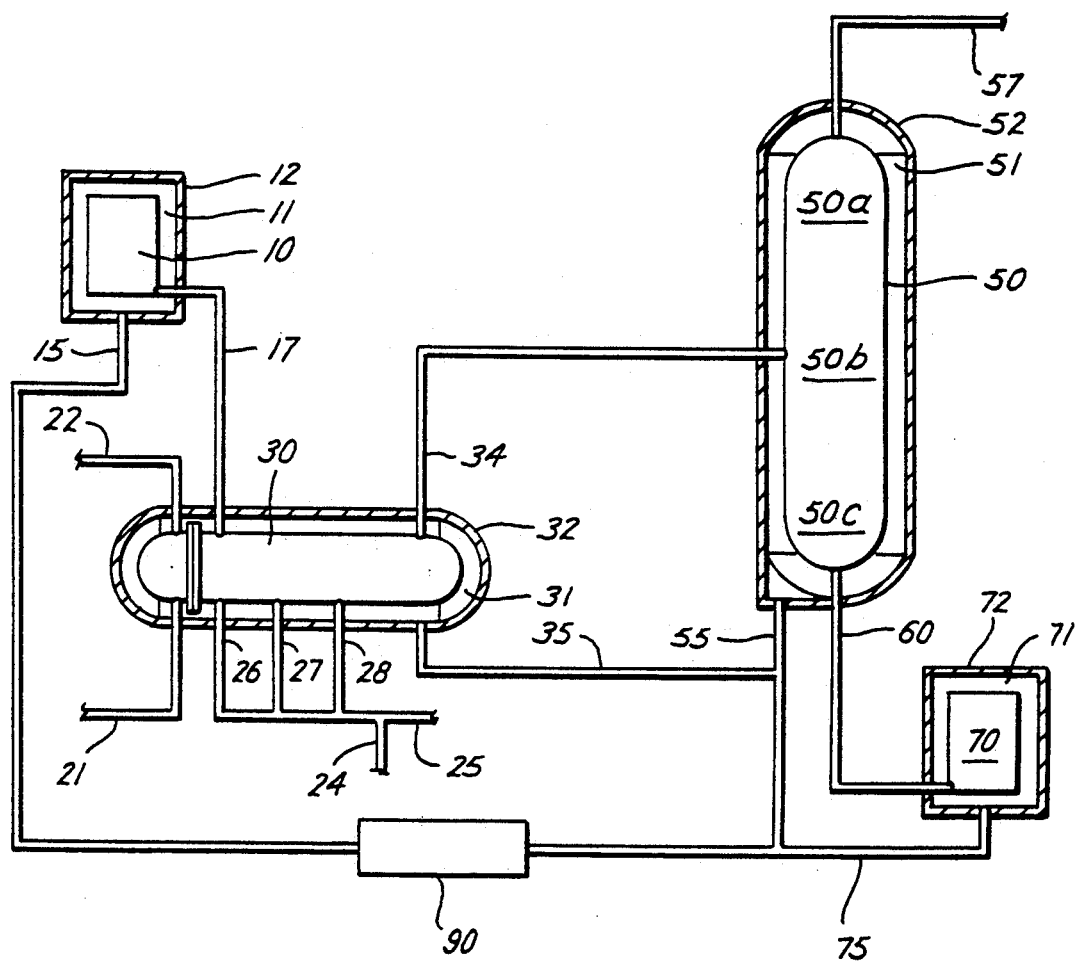

HYDROGEN FLUORIDE ALKYLATION APPARATUS AND VAPOR RECOVERY METHOD

BACKGROUND OF THE INVENTION

1. Field Of The Invention

This invention is an apparatus for carrying out the hydrogen fluoride catalyzed alkylation of hydrocarbons. The apparatus comprises safety baffles which are capable of mitigating the airborne release of hydrogen fluoride should a major process vessel leak occur.

2. Description Of The Related Art

The catalytic alkylation of an isoparaffin with an olefin to produce a branched paraffin is a commercially important process for producing high octane gasoline. In general, the process comprises the reaction of an isoparaffin such as isobutane with an olefin such as propylene, 1-butene, 2-butene or mixtures thereof in the presence of a liquid acid alkylation catalyst in a reaction zone. Reaction is followed by separation of the product and unreacted hydrocarbons from the liquid alkylation catalyst in a settling zone and purification of the alkylate product. If the isoparaffin is isobutane and the olefin is a butene, the alkylate product is isooctane. Alkylate product is used to enhance the octane number of automobile gasoline and aviation gasoline.

Anhydrous hydrogen fluoride is a particularly effective catalyst for the alkylation process. Though effective, the volatility and destructive effect of hydrogen fluoride on animal tissue has curtailed expanded use of this catalyst in the petroleum refining industry due to a concern over accidental releases.

There is a need in the petroleum refining industry for an apparatus to carry out the hydrogen fluoride catalyzed alkylation reaction which will contain an accidental release of hydrogen fluoride from a major process vessel.

SUMMARY OF THE INVENTION

The invention is an apparatus for carrying out the hydrogen fluoride catalyzed alkylation of hydrocarbons. The apparatus comprises a reactor vessel and an acid catalyst settling vessel. Between the reactor vessel and a reactor vessel containment baffle is a first vapor space. Between the settler vessel and a settler vessel containment baffle is a second vapor space.

Mean is provided for transferring fresh hydrogen fluoride to the reactor vessel and for transferring alkylate product from the reactor vessel to an intermediate portion of the acid catalyst settler vessel. An upper portion of the acid catalyst settler vessel has capacity for containing a liquid hydrocarbon phase separated from alkylate product and a lower portion of the acid catalyst settler vessel has capacity for containing a liquid catalyst phase. Means is provided for withdrawing liquid catalyst phase from the lower portion of the acid catalyst settler vessel.

BRIEF DESCRIPTION OF THE DRAWING

The Drawing is a schematic flow diagram illustrating a preferred embodiment of the invention.

DETAILED DESCRIPTION OF THE INVENTION

The alkylation reaction is carried out between an isoparaffin and a monoolefin in the presence of alkylation catalyst. The preferred isoparaffin is isobutane. Isopentane is also used. Common monoolefins include propylene, isobutylene, 1-butene, 2-butene, pentylenes and mixtures thereof. The preferred monoolefin is a $C_4$ olefin, typically a mixture of 1-butene, 2-butene and isobutene. A typical $C_4$ olefin mixture is one fraction from a fluid catalytic cracking process comprising about 25 vol% 1-butene, 45 vol% 2-butene and 30 vol% isobutylene. Diolefins or higher functionality olefins are to be avoided in the reaction. Higher functionality olefins alkylate at each double bond, forming polymers which are not useful for gasoline blending.

The alkylation catalyst is hydrogen fluoride, referred to in the art as hydrofluoric acid or simply by its molecular symbol HF. The hydrogen fluoride is used exclusively in its anhydrous form.

The reaction may be carried out at pressures varying from atmospheric to as high as 1000 psia (68 atm) or higher, preferably about 125 to 220 psia (8.5 to 15 atm) and at residence times of 20 seconds to 5 minutes. The pressure is selected in cooperation with the temperature to maintain the hydrocarbon reactants in liquid phase and generally ranges from $-40°$ F. ($-40°$ C.) to about $150°$ F. ($66°$ C.). In the preferred reaction of isobutane with a $C_4$ monoolefins the reaction temperature is between about $60°$ F. ($15°$ C.) and about $100°$ F. ($38°$ C.) and most preferably about $90°$ F. ($32°$ C.).

In the alkylation reaction a substantial molar excess of isoparaffin to olefin is employed to provide an isoparaffin/olefin feed ratio in excess of about 1/1, generally 4/1 to 70/1 and preferably 5/1 to about 20/1.

Reference is made to the Drawing. The isoparaffin feed in line 24 and the olefin feed in line 25 are combined and introduced into reactor vessel 30 via lines 26, 27 and 28. Fresh, anhydrous hydrogen fluoride in tank 10 is passed via line 17 into reactor vessel 30 which is either horizontally or vertically elongated and cylindrical in shape. The volume of anhydrous, liquid hydrogen fluoride exceeds the volume of the isoparaffin and monoolefin mixture. The liquid hydrogen fluoride constitutes a continuous phase in reactor vessel 30 and the hydrocarbon feedstocks constitute a discontinuous phase. Coolant, such as cooling water is passed via line 21 through heat exchanger tubes (not shown) exposed to the reaction mixture in reactor vessel 30, thereby moderating reaction temperature to the selected range. Coolant is discharged via line 22.

Reaction effluent, comprising alkylate product, unreacted isoparaffin and liquid catalyst are withdrawn from reactor vessel 30 via line 34 and discharged into catalyst settler vessel 50 which is vertically elongated and cylindrical in shape. The catalyst settler vessel 50 is comprised of an upper portion 50a, an intermediate portion 50b and a lower portion 50c which allows for separation of the reaction effluent from the alkylation reactor into an upper liquid hydrocarbon phase in upper portion 50a and a lower liquid catalyst phase containing hydrogen fluoride catalyst, acid soluble oil, and water in lower portion 50c. The catalyst settler vessel 50 may contain separation trays and vertical downcomers (not shown) positioned within the vessel to enhance separation.

The alkylate product phase is withdrawn via line 57 and processed by fractional distillation (not shown) to recover unreacted isoparaffin and alkylate product.

The liquid catalyst phase is withdrawn via line 60 and passed to spent acid tank 70.

Surrounding and completely enclosing each of the major process vessels is a containment baffle. The containment baffle allows for a vapor space between the vessel and the baffle. Fresh acid tank 10 is enclosed by containment baffle 12, providing vapor space 11. Reactor vessel 30 is enclosed by containment baffle 32, providing vapor space 31. Acid catalyst settler 50 is enclosed by containment baffle 52, providing vapor space 51. Spent acid tank 70 is enclosed by containment baffle 72, providing vapor space 71.

Each of the vessels is cylindrical in shape as is each containment baffle. Preferably each containment baffle has a cylindrical radius 0.25 inches (0.635 cm) to 36 inches (91.44 cm) greater than the cylindrical radius of the vessel. Should a major process vessel leak, the vapor space provides volume for hydrogen fluoride to collect while limiting escape to the atmosphere. Hydrogen fluoride vapor has been found to condense on the baffle, forming a liquid condensate. The condensate is passed via condensate lines 15, 35, 55 and 75 to vented sump 90 where it is collected. Vapor recoveries of 75% have been demonstrated experimentally.

Each containment baffle is fabricated from mild steel sheets which are cut and bent to shape and fastened together with fastening means. Corrugated galvanized steel sheets provide additional surface area and are therefore preferred. Fastening means include bolts, welds and the like.

U.S. 5,073,674 to Olah incorporated herein by reference in its entirety discloses catalytic alkylation using liquid onium polyhydrogen fluoride complexes. These compositions show less volatility at alkylation conditions than anhydrous hydrogen fluoride. The use of these complexes in combination with the instant containment baffles is the Best Mode for carrying out the invention contemplated by inventors.

The invention is shown by way of Example.

EXAMPLE

A bench scale apparatus was built to quantify the amount of condensate which would result from impacting anhydrous hydrogen fluoride flashed in air on a surface. The apparatus comprised a ⅛ inch stainless steel tube through which a weighted amount of hydrogen fluoride was passed into an air chamber. Three different size air chambers were used of 30 in$^3$, 60 in$^3$ and 3700 in$^3$ volume. Travel distance from release point to impact surface was 0.55 for the 30 in$^3$ chamber, 3 inches for the 60 in$^3$ chamber and 31 inches for the 3700 in$^3$ chamber. Condensate flowed down the wall and dripped into the pan of a recording weighing scale under nitrogen atmosphere. Uncondensed vapor and air were drawn out of the chamber under vacuum.

The apparatus was used to simulate a leak from a process vessel resulting in airborne hydrogen fluoride release. The air chambers were used to simulate the annular space and containment baffle of the invention.

Results of three experimental runs are reported as follows:

| EXAMPLE | CHAMBER VOLUME | CONDENSATE RECOVERED |
|---|---|---|
| 1 | 30 in$^3$ | 75 wt % |
| 2 | 65 in$^3$ | 49 wt % |
| 3 | 3700 in$^3$ | 0.7 wt % to 1.9 wt % |

Ambient Temperature 21° C.
Hydrogen Fluoride Release Temperature 45° C.
Hydrogen Fluoride Release Pressure 100 psig (7.8 atm)

Anhydrous liquid hydrogen fluoride at a temperature of 45° C. and pressure of 100 psig is released into the air chamber at ambient temperature and atmospheric pressure. On release the liquid hydrogen fluoride flashes to form both liquid droplets and vapor which impact the air chamber wall. The chamber wall, which simulates the containment baffle, provides an impact surface for coalescing of hydrogen fluoride droplets. The annular space reduces air exchange with the atmosphere. Auto cooling of the flashing hydrogen fluoride occurs thereby condensing some vapor. The containment vessel contains the collected liquid hydrogen fluoride.

What is claimed is:

1. Apparatus comprising:
   a hydrogen fluoride catalyzed alkylation reactor vessel for producing alkylate product, a reactor vessel containment baffle and a first vapor space therebetween vented to the atmosphere;
   an acid catalyst settler vessel having an upper portion, an intermediate portion and a lower portion, a settler vessel containment baffle and a second vapor space therebetween vented to the atmosphere;
   means for transferring alkylate product from said hydrogen fluoride catalyzed alkylation reactor vessel to the intermediate portion of the acid catalyst settler vessel, the upper portion of the acid catalyst settler vessel having capacity for containing a liquid hydrocarbon phase separated from alkylate product from the hydrogen fluoride catalyzed alkylation reactor vessel and the lower portion of the acid catalyst settler vessel having capacity for containing a liquid catalyst phase separated from alkylate product from the hydrogen fluoride catalyzed alkylation reactor vessel;
   means for providing hydrocarbon feed to the hydrogen fluoride catalyzed reactor vessel;
   means for providing fresh hydrogen fluoride to the hydrogen fluoride catalyzed alkylation reactor vessel;
   means for withdrawing liquid catalyst phase from the lower portion of the acid catalyst settler vessel.

2. The apparatus of claim 1 additionally comprising a sump in liquid flow communication with each of the first vapor space and the second vapor space.

3. The apparatus of claim 1 wherein each of the reactor vessel containment baffle and the settler vessel containment baffle is fabricated from corrugated steel.

4. The apparatus of claim 1 wherein each of the hydrogen fluoride catalyzed alkylation reactor vessel and the reactor vessel containment baffle is cylindrical in shape, the reactor vessel containment baffle having a cylindrical radius 0.25 inches (0.635 cm) to 36 inches (91.44 cm) greater than a cylindrical radius of the hydrogen fluoride catalyzed alkylation reactor.

5. The apparatus of claim 1 wherein each of the acid catalyst settler vessel and the settler vessel containment baffle is cylindrical in shape, the settler vessel containment baffle having a cylindrical radius 0.25 inches (0.635 cm) to 36 inches (91.44 cm) greater than a cylindrical radius of the acid catalyst settler vessel.

6. Apparatus comprising:
   a hydrofluoric acid catalyzed alkylation reactor for producing alkylate product, a reactor containment baffle and a first vapor space therebetween vented to the atmosphere;
   an acid catalyst settler having an upper portion, an intermediate portion and a lower portion, a settler containment baffle, and a second vapor space therebetween vented to the atmosphere;

means for transferring alkylate product from said hydrofluoric acid catalyzed alkylation reactor to the intermediate portion of the acid catalyst settler, the upper portion of the acid catalyst settler having capacity for containing a liquid hydrocarbon phase separated from alkylate product from the hydrofluoric acid catalyzed alkylation reactor and the lower portion of the acid catalyst settler having capacity for containing a liquid catalyst phase separated from alkylate product from the hydrofluoric acid catalyzed alkylation reactor;

a fresh acid tank containing fresh hydrofluoric acid, a fresh acid tank containment baffle, and a third vapor space therebetween vented to the atmosphere;

means for providing hydrocarbon feed to the hydrogen fluoride catalyzed reactor vessel;

means for transferring fresh hydrofluoric acid from the fresh acid tank to the hydrofluoric acid catalyzed alkylation reactor;

a spent acid tank, a spent acid tank containment baffle, and a forth vapor space therebetween vented to the atmosphere;

means for transferring the liquid catalyst phase from the lower portion of the acid catalyst settler to the spent acid tank.

7. The apparatus of claim 6 additionally comprising a sump in liquid flow communication with each of said first vapor space, second vapor space, third vapor space and fourth vapor space.

8. The apparatus of claim 6 wherein each of said reactor containment baffle, settler containment baffle, fresh acid tank containment baffle, and spent acid tank containment baffle is fabricated from corrugated steel.

9. The apparatus of claim 6 wherein each of the hydrofluoric acid catalyzed alkylation reactor and reactor containment baffle is cylindrical in shape, the reactor containment baffle having a cylindrical radius 0.25 inches (0.635 cm) to 36 inches (91.44 cm) greater than a cylindrical radius of the hydrofluoric acid catalyzed alkylation reactor.

10. The apparatus of claim 6 wherein each of the acid catalyst settler and the settler containment baffle is cylindrical in shape, the settler containment baffle having a cylindrical radius 0.25 inches (0.635 cm) to 36 inches (91.44 cm) greater than a cylindrical radius of the acid catalyst settler.

11. The apparatus of claim 6, wherein each of the fresh acid tank and the fresh acid tank containment baffle is cylindrical in shape, the fresh acid tank containment vessel having a cylindrical radius 0.25 inches (0.635 cm) to 36 inches (91.44 cm) greater than a cylindrical radius of the fresh acid tank.

12. The apparatus of claim 6 wherein each of the spent acid tank and the spent acid tank containment baffle is cylindrical in shape, the spent acid tank containment vessel having a cylindrical radius 0.25 inches (0.635 cm) to 36 inches (91.44 cm) greater than a cylindrical radius of the spent acid tank.

13. The apparatus of claim 6 wherein the fresh hydrofluoric acid is a liquid onium polyhydrogen fluoride complex.

* * * * *